United States Patent
Fernandes et al.

(10) Patent No.: US 7,971,715 B1
(45) Date of Patent: Jul. 5, 2011

(54) MEDICAL DISPOSABLES CONTAINERS

(75) Inventors: Craig Fernandes, Knoxville, TN (US);
Terry B. Kehne, Knoxville, TN (US);
Gary F. Peters, Knoxville, TN (US);
William G. Pittman, Knoxville, TN (US); E. Steven Ward, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 1979 days.

(21) Appl. No.: 10/988,992

(22) Filed: Nov. 15, 2004

(51) Int. Cl.
*B65D 83/10* (2006.01)

(52) U.S. Cl. ............ 206/366; 206/459.1; 116/100; 340/568.1

(58) Field of Classification Search ............. 206/366, 206/459.1; 116/100, 204; 340/568.1
See application file for complete search history.

(56) References Cited

U.S. PATENT DOCUMENTS

| 2,797,405 | A | * | 6/1957 | Stelter | 340/570 |
| 4,204,632 | A | * | 5/1980 | Cook | 232/34 |
| 4,715,498 | A | | 12/1987 | Hanifl | |
| 4,903,832 | A | * | 2/1990 | Stewart | 206/366 |
| 5,240,108 | A | | 8/1993 | Tonna | |
| 5,387,735 | A | | 2/1995 | Ponsi et al. | |
| 5,388,570 | A | * | 2/1995 | Wassil | 128/200.24 |
| 5,915,558 | A | * | 6/1999 | Girvetz | 206/534 |
| 5,918,739 | A | | 7/1999 | Bilof et al. | |
| 5,947,285 | A | * | 9/1999 | Gaba et al. | 206/366 |
| 7,116,224 | B2 | * | 10/2006 | Mickler | 340/568.1 |

* cited by examiner

*Primary Examiner* — Jacob K Ackun, Jr.
(74) *Attorney, Agent, or Firm* — Luedeka, Neely & Graham, PC

(57) ABSTRACT

A disposal system including a container having a door movable between a first position and a second position for introducing material to be disposed into the container, and a sensing system operatively associated with the container to sense the position of the door and to generate an alarm signal in response to a predetermined position of the door.

4 Claims, 3 Drawing Sheets

MEDICAL DISPOSABLES CONTAINERS

FIELD OF THE INVENTION

The invention relates generally to disposable containers for medical sharps. More particularly, the invention relates to disposable containers for medical sharps and to devices for modifying conventional containers which result in containers having safety features that help to avoid overfilling of containers and the disadvantages associated therewith.

BACKGROUND OF THE INVENTION

In the medical field, the disposal of medical sharps waste is a known hazard. There are a large number of areas in a given healthcare provider environment where sharp medical devices are used and once used, the disposal of the soiled sharp represents a relatively hazardous activity. A large number of products have evolved to address these issues.

Perhaps one of the areas of most concern is where unsupervised non-professionals and patients overlap with the provision of healthcare services. In these areas, the hazard in multiplied due to the fact that many non-professionals are not fully informed of the hazardous nature of contaminated medical sharps, are not on guard to the potential hazards and healthcare professionals may be distracted by the interface with patients and/or visitors. A good example of this environment is the hospital room or the examination room in a doctor's office. In this environment, use of medical sharps is routine, as for administering medication through an I.V. or hypodermic syringe and often patients and other non-professionals are left unsupervised for periods of time. In this context, the question of what to do with the used sharp arises.

One option would be to remove the used sharp from the room; however, such an option as been determined to be unsatisfactory, since the transport of the used sharp to another location results in more exposure to the hazard. The preferred option is to dispose of the sharp in a location proximal to its use, thus minimizing any transport hazard.

The proximal disposal of sharps in patient rooms has spawned a host of specialized sharps disposal containers. These containers are primarily designed to allow for the easy disposal of a sharp in a manner that doesn't require excess effort or exposure to the sharp portion of the device and in which the disposed of sharp cannot be subsequently accessed. In most instances, the disposal device consists of a non-disposable cabinet or support that is more or less permanently affixed to a surface in the room (usually affixed to the wall with some type of anchor such as screws) and a disposable container that fits within or is attached to the cabinet or support.

Typically, the disposable container utilizes some type of door that prevents unobstructed access to the interior of the container, but allows relatively easy disposal of the sharp. For example, mailbox style doors are quite common in which the door incorporates an area to place a used sharp. Once the used sharp is placed in position, the door is moved to a second position in which the sharp is dropped into the interior of the container. In this manner, the interior of the container is never completely open to the room and the sharp can be disposed of with one simple motion. In some mailbox door versions of a container, the door is counterbalanced so that the user never need operate the door, the weight of the sharp on the door caused the door to rotate and drop the sharp and, once dropped the door returns to the ready for use position.

In addition to a safety door mechanism, most in room sharps containers also incorporate some mechanism for insuring that the sharp, once disposed, cannot be retrieved. Often this mechanism is a tortuous path that the sharp follows into the interior of the container. This path typically reduces the chances that the sharp can be returned to an area proximal the door and also prevents the entrance of hands and fingers into the interior of the container where the disposed of sharps reside. Often, this path is designed cooperatively with the safety door to provide further protection and avoid access to the interior of the container.

As a final safety feature, many in-room sharps containers incorporate automatic, mechanical full indications. Obviously, if the container is overfilled, it is likely that one or more of the safety mechanisms described above will not function properly. For example, if a container is overfilled, the tortuous path might back up and allow contaminated sharps to remain proximate the opening or even protrude through the opening allowing for the opportunity for injury. Alternative, the overfilled container might prevent closing of the safety door, allowing a sharp to protrude from the opening and, again, provide an opportunity for sharps injury. In many of the in-room units, the geometry of the safety door and the interior access prevention geometry cooperate such that when the container is filled (or overfilled), the last sharp will obstruct the return path of the safety door thus holding it in a closed position. Often, this portion of the door is also provided with visual indicia to indicate that the container is full. Thus, the healthcare provide only need secure the lock on the container, remove it from the permanent fixture and dispose of it properly.

Despite all of the above-described safety features, thousands of patients and healthcare workers are injured by contaminated sharps in patient rooms every year. Although there are a number of causes, a large number of such injuries are the result of the interface with the in room sharps disposal containers and, a significant percentage, if not majority, are due to continued use or attempted use of filled or overfilled containers.

SUMMARY OF THE INVENTION

The invention relates to a disposal system that is particularly suitable for use in disposal of medical sharps. The system includes a container having a door movable between a first position and a second position for introducing material to be disposed into the container, and a sensing system operatively associated with the container to sense the position of the door and to generate an alarm signal in response to a predetermined position of the door.

The sensing system includes a proximity element and a sensing unit positioned to detect the presence of the proximity element based on the position of the door. When the proximity element is not within a predetermined relationship relative to the sensing unit, such as not being within a predetermined distance of the sensing unit, the sensing system generates an alarm signal.

BRIEF DESCRIPTION OF THE DRAWINGS

Further advantages of the invention will become apparent by reference to the detailed description of preferred embodiments when considered in conjunction with the drawings, wherein like reference characters designate like or similar elements throughout the several drawings as follows.

DETAILED DESCRIPTION

Figure 1:
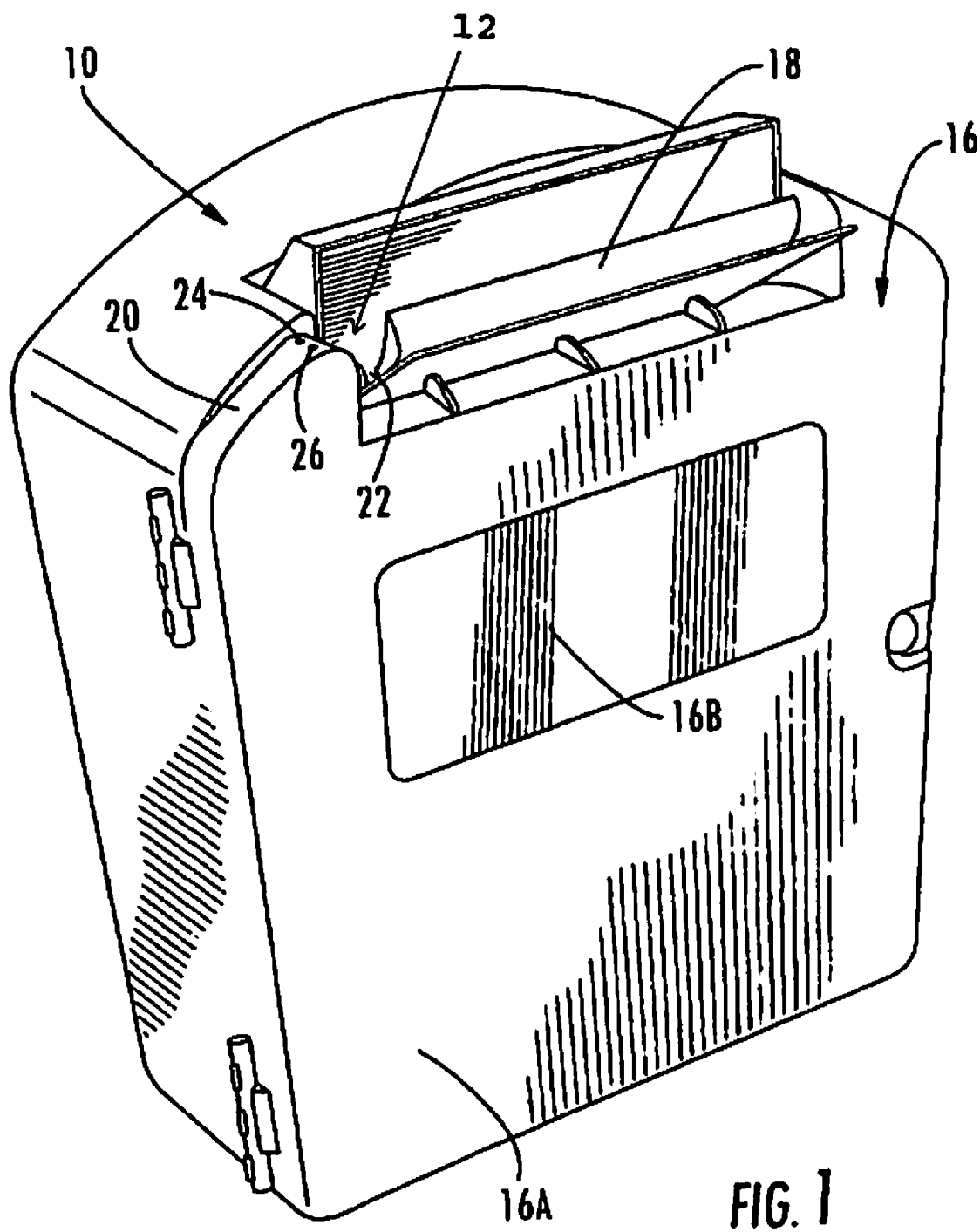
FIG. 1 is a perspective view of a medical sharps system according to a preferred embodiment of the invention.
Figure 2:
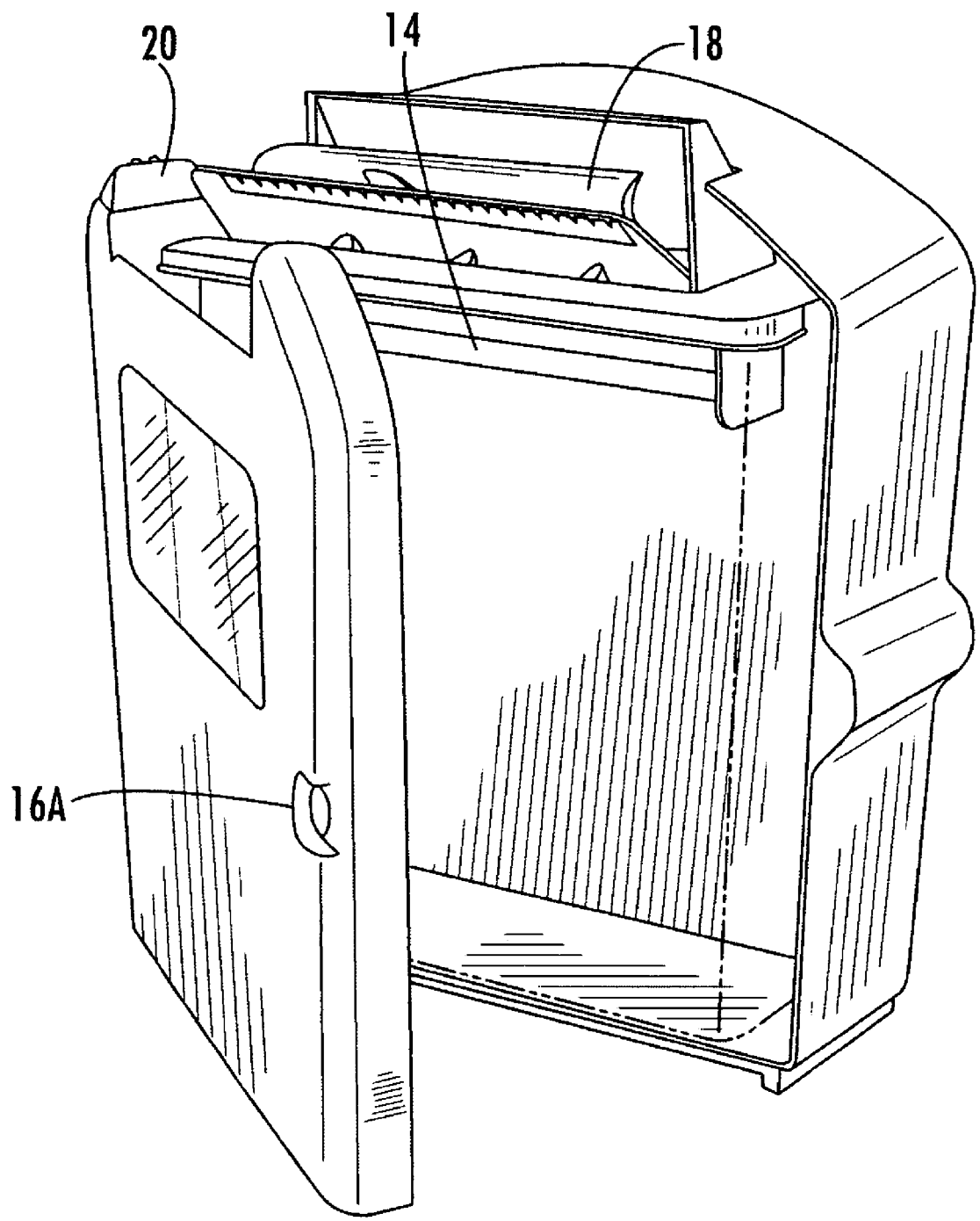
FIG. 2 shows the system of FIG. 1 with the door thereof open.
Figure 3:
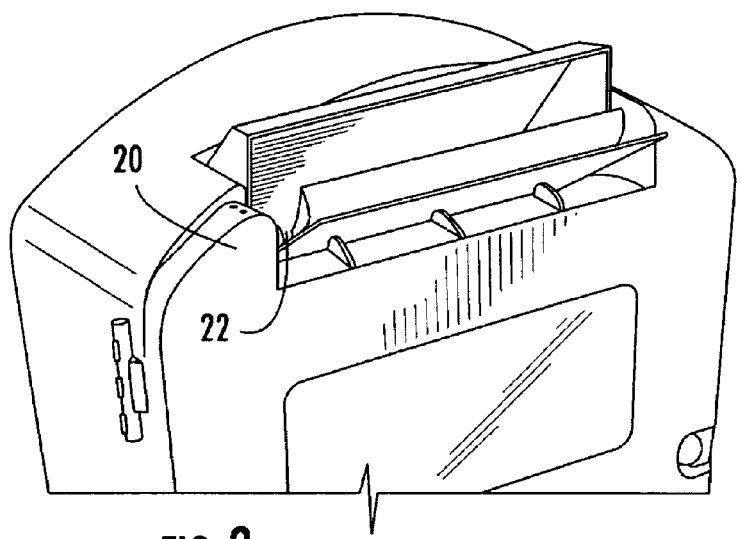
FIG. 3 is a close-up view of a portion of the system of FIG. 1 showing a sensor thereof.
Figure 4:
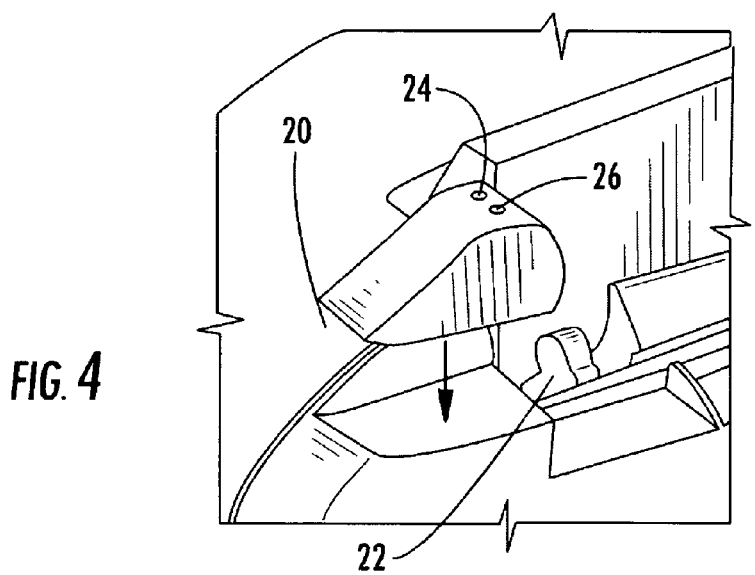
FIG. 4 is an enlarged view of a portion of FIG. 3.

Similar to the situation with someone drinking the last cup of coffee in an office and not making more, the filled in room sharps container represents a dilemma in the health care environment. Despite numerous safety advances in the containers, healthcare workers and, less often, non-professionals continue to be injured by sharps. In many instances the injuries are the result of the overfilling of the sharps container. One common occurrence is that the last person to make use of sharps container who is responsible for the container becoming full often does not realize that fact, or forgets to note the fact and have the container changed. The next healthcare worker that enters the room then proceeds to use a sharp in the care of the patient and when they try to dispose of the sharp, they find the container full. Often, they will try to force the sharp into the container, or will further handle the sharp since the container is full and will suffer a sharps injury. Alternatively, the overfilled container does not allow for the complete disposal of the last sharp and a patient or other non-professional in the room can obtain access to the sharp and that person is injured.

In this regard, and in accordance with a first aspect of the invention, the invention relates to devices for use with disposable sharps containers of the type that utilize a mechanical full position safety door. In these devices, the door regulating access to the interior of the container typically has two positions with the first being a ready for use position and the second being a disposing/full position. In such units, when the unit is full, the door is prevented or obstructed from returning to the ready for use position.

The systems of the present invention are configured to provide auditory and/or visual warnings to indicate when the container should be changed. For example, while the person who is responsible for the filling the container with the last sharp might not notice that the safety door hasn't returned to the ready to use position, activation of an auditory signal or warning light facilitates recognition of this condition so that the personnel may take action to result in removal of the full container. Similarly, if the container were not changed prior to the next use, the visual and/or auditory warnings will be present to alert subsequent personnel to the full condition of the container prior to their utilization of a medical sharp and the commensurate creation of a hazardous exposed sharp situation.

In accordance with a preferred embodiment, and with reference to FIGS. 1-5, the foregoing aspects of the invention are preferably achieved by the provision of system 10 having a sensing system 12 disposed in cooperation with a sharps disposal container 14 positionable within a cabinet or support 16. The sensing system 12 is adapted to sense the position of a door 18 of the disposable container 14 and, if it senses the door 18 in the full position (as opposed to the ready to use position) it alarms and provides a signal indicating that the disposable container needs to be removed. The cabinet 16 preferably includes a hinged access door 16a having a viewing window 16b.

The sensing system 12 may preferably include a sensing unit 20 and a proximity element 22. In operation, the sensing unit 20 is designed to detect the presence of the proximity element 22. In the event that the proximity element 22 is not within a specified distance of the sensing unit 20, the sensing unit generates and alarm signal. The proximity element 22 may preferably be provided as by a magnet and the sensing unit 20 provided by a magnet sensor. When the magnet and the sensor are removed from a proximal relationship, the sensing unit 20 provides an alarm signal. In the case of the sharps disposal container 14, the sensor unit 20 may be permanently or removably mounted on the cabinet or support 16 and the proximity element 22 is positioned on the door 18. The sensing unit 20 is powered as by a source of electrical power such as a battery.

The system 12 is preferably configured so that when the container door 18 is in the ready to use position, the proximity element 22, such as a magnet, and the sensing unit 20, such as a magnet sensor, are sufficiently proximate and no alarm signal is present, or else a "good" condition indication is supplied. For example, the sensing unit 20 may illuminate a green light emitting diode (LED) 24 to indicate the container is usable and not full. However, when the door 18 is not in the ready to use position, the proximity element 18 is no longer proximate the sensing unit 20 and the sensing unit 20 generates an alarm signal, preferably resulting in the illumination of a red LED 26 associated therewith to indicate the full or unusable condition. Electronics associated with the sensing unit 20 may utilize the alarm signal to provide further notification of the full condition of the container 14 such as an auditory and/or visual indicator and/or communicate with a remote location as by connection to a phone line or other wired or wireless communication device.

Figure 5:
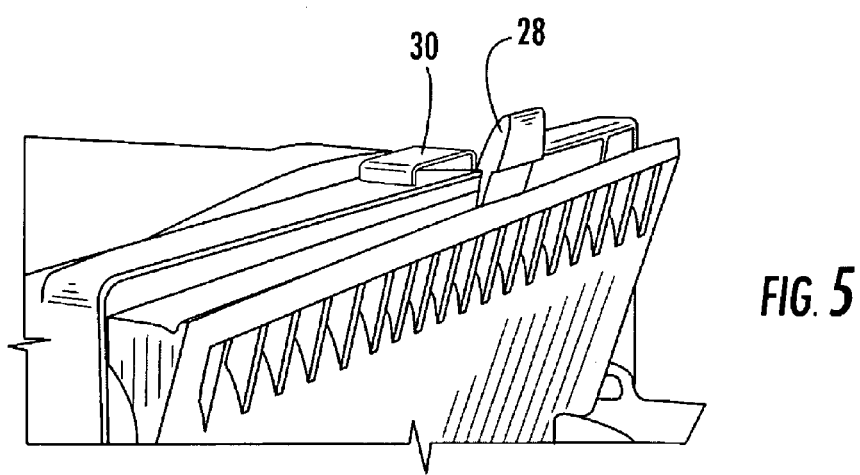
FIG. 5 shows a preferred lock component of the system of FIG. 1.

With reference to FIG. 5, the door 18 of the container 14 also preferably includes a tab 28 which is non-removably insertable into a corresponding receiver 30 located on the container 14 to lock the door 18 so that it cannot be opened. Thus, when the red LED or other full indicator is activated in indication of a full condition of the container, the user may lock the container 14 by use of the tab 28 and the receiver 30.

In an alternate embodiment, the sensing unit 20 may be provided by an optical sensing unit and the proximity element 22 may be an optical proximity element. For example, the sensing unit 20 may incorporate a light emitting element, such as light bulb, light emitting diode, or, solid state laser element, in conjunction with a light detector. Correspondingly, the proximity element 22 may be provided as by a light reflecting element, such as a reflector. In this embodiment, when the door is in the ready to use position, the light from the light-emitting element is reflected off the reflector and onto the light sensor providing a signal with a minimum strength. When the door is located in a position other than the ready to use position such that the reflector is out of position and remote, the amount of light reaching the detector is reduced to a level below a predetermined minimum level, thus resulting in an alarm signal.

Alternatively, the proximity element 22 may be a light emitting element, such as a relatively low power LED. In such cases, the sensing unit 20 may include an optical detector and a tab structure may be provided on the door to interrupt the light beam when the door is not in the ready-to-use position. Thus, when the beam remains interrupted, the sensing unit 20 will generate one or more alarm signals in response.

The proximity element 22 may also be provided as by radio frequency (RF) transponders, with the sensing unit 20 including an RF sensor and a low power RF transmitter in the sensing unit. In such a configuration, the signal transmitted by the transmitter will be received by the transponder when the proximity element is within range. This results in the transmission of an RF signal by the transponder that is subsequently received by the sensing unit. By selecting the appropriate parameters, the transponder in the proximity element will only be activated when that transponder is within a certain range of the sensing unit, thus allowing the use of the transponder as a proximity element. The use of an RF system has further potential benefits as well. RF transponders can typically be encoded with a unique response signal so that every container could have a unique identification. In that context, the RF transponder proximity element could also function as an inventory control and waste-tracking device, and to collect information relating to the usage levels associated with disposable containers in certain location.

The proximity unit 22 may also be provided as by a switch activated by the position of the container door 18 and the sensing unit 20 provided as by circuitry operatively connected to the switch to determine the state of the switch, and thus whether the door 18 is open or closed. The switch may preferably be a microswitch imbedded on the cabinet/support 16 that is contacted when the door 18 is in the closed/full condition (or alternatively the open position) and including logic circuitry that provides the desired alarm signal. For example, when the door 18 is in the ready to use or open position, the door 18 or a tab on the door contacts the switch. The switch is wired to circuitry having logic operable to time the out of contact condition and generate an alarm signal after a predetermined time period, essentially detecting the absence of the door at the selected position or other predetermined relationship. Alternatively, the switch could be closed when the door 18 is in the full/closed position.

In regard to the foregoing embodiments, it will understood that the positions of the sensing unit 20 and the proximity unit 22 may be reversed, such that the sensing unit 20 is located on the container door 18 and the proximity element 22 is located on the cabinet/support 16. Accordingly, it will be appreciated that regardless of the orientation, the failure of the door 18 to return to the ready to use position results in an alarm or other signal triggering event.

With regard to the foregoing, it will be further understood that the alarm/signal may be represented by any electronic or electrical indication generated in response to the door 18 being out of the ready to be used position and may, for example, be analog or digital signal, and may be a high or low value signal or, in the case of an analog signal, may be a signal whose strength is proportional to the distance from the proximity element 22 to the sensing unit 20.

For example, in the utilization of relatively simple electronic circuitry, the alarm signal generated in response to a selected door position may directly trigger an audible alarm, a visual alarm or a combination of both whenever the alarm signal is present (i.e. when the door is not in the ready to use position).

In more complex circuits, logic or delay circuitry may preferably be incorporated into the sensing unit to delay triggering of the actual alarm until the alarm signal is present for some period of time. For example, since in normal operation the proximity element will be non-proximate the sensing unit for the period of time required to cycle the door to allow for the drop of the sharp, the sensing unit may be configured to require that the alarm signal be present for a period of time longer than the normal cycle time so that the unit does not alarm every time a sharp is dropped.

In addition, when a combination of auditory and visual alarms are used, it is preferred that the auditory alarm be triggered only after a delay while the visual indicator is preferably activated whenever the door is not in the ready to use position. In the case of digital circuits, the presence of the alarm signal may be timed to provide a desired delay. In the case of analog circuit, it is preferred to include a delay capacitor or inductor to provide the desired delay.

In addition, the alarm signal may also be utilized for purposes other than simply indicating those proximate to the container that the container is in an overfill condition. For example, the alarm signal may be transmitted, by wire or wireless circuitry, to a remote location to signal the need for intervention regarding the container. The alarm signal may be transmitted to a floor nursing station or an environmental services department of a hospital to be displayed on a computer or monitor to inform personnel of the need to investigate the condition of the container and change it if necessary.

In addition, and particularly in the event an RF transponder is used as the proximity element 22, the signal may be directed to a computer based inventory control systems so that the location of the container 14 may be tracked. For example, a low power RFID interrogator may be used as the proximity sensor module for monitoring the full status of the container while higher powered units may be used to track the locations of the containers.

It is contemplated, and will be apparent to those skilled in the art from the preceding description and the accompanying drawings, that modifications and changes may be made in the embodiments of the invention. Accordingly, it is expressly intended that the foregoing description and the accompanying drawings are illustrative of preferred embodiments only, not limiting thereto, and that the true spirit and scope of the present invention be determined by reference to the appended claims.

What is claimed is:

1. A medical sharps disposal system for disposal of sharps, comprising a container having a mechanical full position safety door movable between a first position and a second position for introducing material to be disposed into the container, the first position being a ready to use position and the second position being a full position corresponding to the container being full of sharps, the door being obstructed from returning to the first position when the container is full of the sharps; and a sensing system operatively associated with the container to sense the position of the door and to generate an alarm signal in response to a predetermined position of the door, the sensing system including a proximity element and a sensing unit positioned to detect the presence of the proximity element based on the position of the door, wherein one of the proximity element or the sensing unit moves with the door when the door is moved and the other is at a fixed location relative to the door and does not move when the door is moved, the positions of the proximity element and the sensing unit being reversible, wherein when the proximity element does not correspond to a predetermined relationship relative to the sensing unit, the sensing system generates an alarm signal.

2. The system of claim 1, wherein when the door is in the ready to use orientation corresponding to the first position, the proximity element and the sensing unit are sufficiently proximate to one another so as to be within a predetermined distance corresponding to the predetermined relationship.

3. The system of claim 1, wherein the proximity element comprises a magnet and the sensing unit comprises a magnet sensor.

4. The system of claim 1, wherein the predetermined relationship comprises the proximity element and the sensing unit being sufficiently proximate to one another so as to be within a predetermined distance.

\* \* \* \* \*